(12) United States Patent
Heckmann et al.

(10) Patent No.: US 7,285,663 B2
(45) Date of Patent: Oct. 23, 2007

(54) β-ISOINDIGO COLORING AGENT

(75) Inventors: Heino Heckmann, Liederbach (DE); Hans Joachim Metz, Darmstadt (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 0 days.

(21) Appl. No.: 10/542,529

(22) PCT Filed: Dec. 13, 2003

(86) PCT No.: PCT/EP03/14201

§ 371 (c)(1),
(2), (4) Date: Jul. 15, 2005

(87) PCT Pub. No.: WO2004/065490

PCT Pub. Date: Aug. 5, 2004

(65) Prior Publication Data

US 2006/0041034 A1 Feb. 23, 2006

(30) Foreign Application Priority Data

Jan. 21, 2003 (DE) .............................. 103 02 020

(51) Int. Cl.
*C07D 403/10* (2006.01)
*C09D 11/02* (2006.01)
*C09B 7/02* (2006.01)
(52) U.S. Cl. .................. 544/296; 523/161; 548/457
(58) Field of Classification Search ................ 548/490, 548/457; 544/296; 523/161
See application file for complete search history.

(56) References Cited

U.S. PATENT DOCUMENTS 2,254,354 A * 9/1941 Davies ................... 548/364.7
4,564,680 A 1/1986 Rolf et al.
4,707,548 A 11/1987 Lotsch et al.

FOREIGN PATENT DOCUMENTS

EP 0101954 8/1982
EP 0190692 8/1986

OTHER PUBLICATIONS

English Translation of PCT IPER for PCT/EP03/14201, Sep. 22, 2005.
PCT IPER for PCT/EP 03/14201, Sep. 22, 2005.
PCT Search Report for PCT/DP 03/14201, May 7, 2004.
R.P. Smirnov et al., "Synthesis and Study of Properties of Macrocycles, I. Reaction of Diamio-β-isoindigo with salts of hydrazine." Vysshikh, Uchebn. zavednii, Khim. I Khim Tekhnol. No. 6 pp. 1022-1024 (1963) AND English Abstract.

* cited by examiner

*Primary Examiner*—Kamal A. Saeed
*Assistant Examiner*—Joseph R. Kosack
(74) *Attorney, Agent, or Firm*—Anthony A. Bisulca

(57) ABSTRACT

The invention relates to a compound of general formula (I) in which C represents an alicyclic or heterocyclic group having $C_{2v}$ symmetry, and B represents ortho-$C_6$-$C_{18}$-arylene. The invention also relates to a method for producing this compound and to the use thereof as a coloring agent for coloring or pigmenting organic or inorganic high-molecular or low-molecular, particularly high-molecular, organic materials (I)

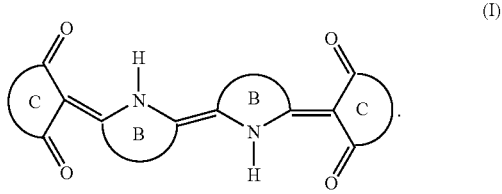

9 Claims, No Drawings

β-ISOINDIGO COLORING AGENT

The present invention relates to new organic pigments and dyes.

In the field of colorants there is a continual market demand for new color shades possessed of high migration fastness and light fastness properties, good heat stabilities and high tinctorial strength, and also, in the case of pigments, high solvent fastness properties.

U.S. Pat. No. 2,254,354 describes β-isoindigo compounds which are substituted by a cyclic radical that contains at least one =CH$_2$—CO— group. The compounds specified therein, however, are dull.

An object which existed was to provide improved β-isoindigo pigments which besides the abovementioned pigmentary properties are possessed of higher cleanness and brightness than those in the prior art.

It has been found that this object is achieved, surprisingly, by compounds of the formula (I).

The present invention accordingly provides compounds of the formula (I)

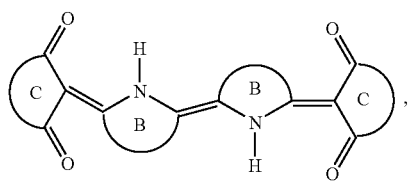

(I)

where C is an alicyclic or heterocyclic group having $C_{2v}$ symmetry and B is ortho-$C_6$-$C_{18}$ arylene.

Preferably the compounds of the formula (I) are symmetrical, i.e. the groups B are each identical and the groups C are each identical.

Preference is also given to compounds of the formula (I) in which B is ortho-phenylene or 2,3-naphthylene.

Preference is additionally given to compounds of the formula (I) in which the ring C corresponds to a ring system having $C_{2v}$ symmetry of the formulae (a) to (d)

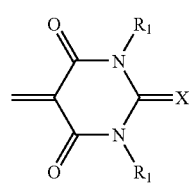

(a)

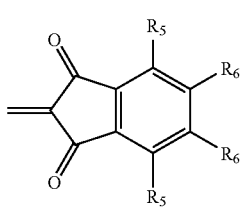

(b)

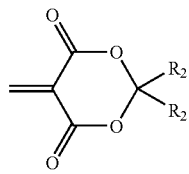

(c)

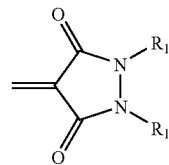

(d)

where $R_1$ and $R_2$ independently of one another are hydrogen, $C_1$-$C_{25}$ alkyl, $C_5$-$C_{12}$ cycloalkyl, $C_6$-$C_{24}$ aryl, $C_1$-$C_{25}$ alkyl-($C_6$-$C_{10}$)-aryl, a heteroaromatic radical having 1, 2 or 3 heteroatoms from the group N, O and S, —(CH$_2$)$_n$—COR$_3$ or —(CH$_2$)$_m$—OR$_4$, in which $R_3$ is hydroxyl, unsubstituted or mono- or poly-hydroxyl- or amino-substituted $C_1$-$C_{25}$ alkoxy, $C_1$-$C_{25}$ alkylamino, di-($C_1$-$C_{25}$ alkyl)amino, $C_1$-$C_{25}$ alkyl-$C_6$-$C_{24}$ arylamino, ($C_6$-$C_{24}$ aryl)amino, di-($C_6$-$C_{24}$ aryl)amino or $C_2$-$C_{24}$ alkenyloxy, and $R_4$ is hydrogen or —CO—($C_1$-$C_{25}$ alkyl), and n and m independently of one another are an integer from 0 to 6, preferably 1 to 4, and in which in $R_1$, $R_2$, $R_3$ and $R_4$ a C—C unit may also be replaced by an ether unit C—O—C, and X is =O, =S or =NR$_2$, and $R_5$ and $R_6$ independently of one another are hydrogen, halogen, CN, $R_1$, OR$_1$, SR$_1$, NR$_1$R$_2$, NO$_2$, SO$_2$(OR$_1$), SO$_2$R$_1$, SO$_2$NR$_1$R$_2$ or PO$_2$(OR$_1$). The concept of $C_{2v}$ symmetry is described in the technical literature.

The substituents C in compounds of the formula (I), as $C_{2v}$-symmetric molecules, possess the symmetry elements of the identity, one $C_2$ axis and two mirror planes which are orthogonal to one another and whose intersect gives the $C_2$ axis.

$R_1$ and R2 are more preferably hydrogen, $C_1$-$C_{18}$ alkyl, $C_5$-$C_6$ cycloalkyl, $C_6$-$C_{10}$ aryl, benzyl, pyridyl, pyrryl, thienyl, imidazolyl, oxazolyl, thiazolyl, pyrimidyl, hydroxycarbonyl-$C_0$-$C_{18}$ alkyl, $C_1$-$C_{18}$ alkoxycarbonyl-$C_0$-$C_{18}$ alkyl, aminocarbonyl-$C_0$-$C_{18}$ alkyl, $C_1$-$C_{18}$ alkylaminocarbonyl-$C_0$-$C_{18}$ alkyl, $C_6$-$C_{10}$ arylaminocarbonyl-$C_0$-$C_{18}$ alkyl, di($C_1$-$C_{18}$ alkyl)amino-carbonyl-$C_0$-$C_{18}$ alkyl, $C_1$-$C_{18}$ alkyl-$C_6$-$C_{10}$-arylaminocarbonyl-$C_0$-$C_{18}$ alkyl and di($C_6$-$C_{10}$-aryl) aminocarbonyl-$C_0$-$C_{18}$ alkyl.

$R_3$ is more preferably hydroxyl, $C_1$-$C_{18}$ alkoxy, $C_1$-$C_{18}$ alkylamino, di($C_1$-$C_{18}$ alkyl)amino, benzylamino, $C_6$-$C_{10}$ arylamino, di($C_6$-$C_{10}$-aryl)-amino or ($C_2$-$C_{18}$) alkenyloxy.

$R_5$ and $R_6$ are more preferably hydrogen, Cl, Br, $C_1$-$C_{18}$ alkyl, $C_5$-$C_6$ cycloalkyl, benzyl, $C_6$-$C_{10}$ aryl, pyridyl, pyrryl, thienyl, imidazolyl, oxazolyl, thiazolyl, pyrimidyl, $C_1$-$C_{18}$ alkoxy, $C_6$-$C_{10}$ aryloxy, $C_1$-$C_{18}$ alkylthio, $C_6$-$C_{10}$ arylthio, $C_1$-$C_{18}$ alkylamino, $C_6$-$C_{10}$ arylamino, di($C_1$-$C_{18}$ alkyl)-amino, $C_1$-$C_{18}$ alkyl-$C_6$-$C_{10}$-arylamino, di($C_6$-$C_{10}$-aryl) amino, SO$_3$H, $C_1$-$C_{18}$ alkoxysulfonyl, $C_1$-$C_{18}$ alkylsulfonyl and di($C_1$-$C_{18}$ alkyl)aminosulfonyl.

Of particular interest are the compounds of the formula (2) and (3)

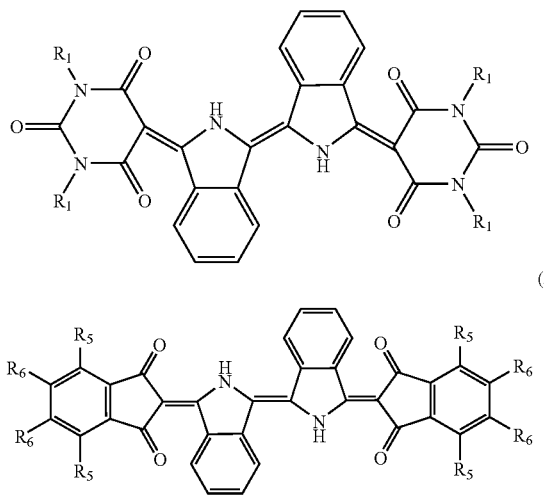

(2)

(3)

in which $R_1$, $R_5$ and $R_6$ are as defined above.

The present invention further provides a process for preparing compounds of the formula (I) by condensing a compound of the formula (III)

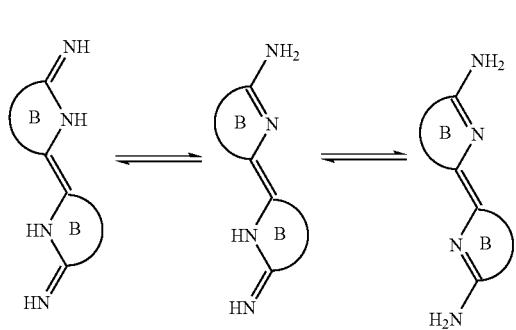

(III)

with at least 2 mole equivalents of a cyclic compound of the formula (IV)

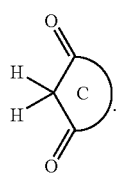

(IV)

Appropriately the reaction takes place at a temperature of 10 to 250° C., preferably 100 to 200° C., preferably in a high-boiling solvent, such as N-methylpyrrolidone, propylene glycol, 2-phenoxyethanol, chlorobenzene, 1,2-dichlorobenzene, 1-chloronaphthalene, N,N-dimethylaniline, and also, if desired, in the presence of an organic acid, such as formic acid, acetic acid and propionic acid, for example, or in the presence of an inorganic acid, such as sulfuric acid, hydrochloric acid and phosphoric acid, for example.

The compounds of the formula (III) can be prepared by a process known per se (R. P. Smirnov et al, Izv. Vysshikh, Uchebn.Zavednii, Khim. i Khim. Tekhnol. 1963, 6, 1022-4) by reacting [1,1']biisoindolylidene-3,3'-dithiones of the formula (V) with concentrated aqueous ammonia solution in an autoclave in the presence of sodium nitrite at 110° C.

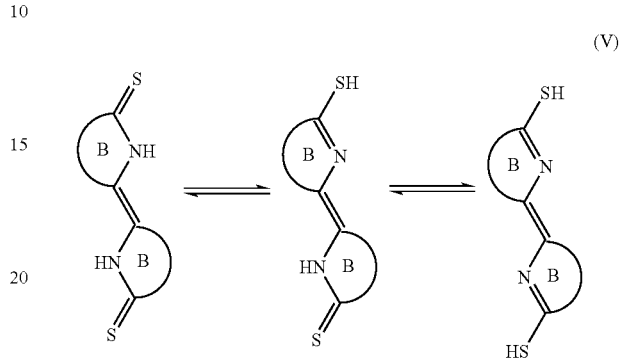

(V)

Compounds of the formula (I) according to the invention are used for coloring or pigmenting organic or inorganic materials of high or low molecular mass, especially organic materials of high molecular mass.

Depending on the nature of their substituents and of the high molecular mass organic material to be colored, the compounds of the invention may be used as polymer-soluble dyes or as pigments. In the latter case it is advantageous to convert the as-synthesized products (crude pigments) into a finely disperse form having often further-improved pigment properties, by aftertreatment in organic solvents in which the pigments themselves are not dissolved, and at elevated temperatures, for example at 60 to 200° C., in particular at 70 to 150° C., preferably at 75 to 100° C. The aftertreatment is preferably combined with a grinding or kneading operation.

The colorants of the invention are outstandingly suitable for coloring high molecular mass materials, which may be organic or inorganic in nature, and plastics and/or natural materials. These may be, for example, natural resins, drying oils, rubber or casein. Alternatively they may be modified natural materials, such as chlorinated rubber, oil-modified alkyd resins, viscose, cellulose derivatives, such as cellulose esters or cellulose ethers, and, in particular, synthetic organic polymers (plastics), which may be obtained by addition polymerization, polycondensation or polyaddition. From the class of the plastics prepared by addition polymerization mention may be made in particular of the following: polyolefins, such as polyethylene, polypropylene, polyisobutylene, and substituted polyolefins such as polystyrene, polyvinyl chloride, polyvinylidene chloride, polyvinylacetals, polyacrylonitrile, polyacrylic acid, polymethacrylic acid, polyacrylic esters and polymethacrylic esters or polybutadiene, for example, and also copolymers thereof.

From the class of the plastics prepared by polyaddition and polycondensation mention may be made of the following: polyesters, polyamides, polyimides, polycarbonates, polyurethanes, polyethers, polyacetals, and also the condensation products of formaldehyde with phenols (phenolic resins) and the condensation products of formaldehyde with urea, thiourea, and melamine (amino resins). The materials in question may also be silicones or silicone resins.

High molecular mass materials of this kind can be present individually or in mixtures in the form of plastic masses or melts or in the form of spinning solutions. They may also be present in the form of their monomers or in the polymerized state, in dissolved form, as film formers or binders for paints or printing inks, such as linseed oil varnish, nitrocellulose, alkyd resins, melamine resins and formaldehyde resins or acrylic resins.

The compounds of the invention are suitable, accordingly, as colorants in oil-based or water-based paints, in coating materials of various kinds, camouflage paints, for spin coloring, for the mass coloring or pigmenting of plastics, in printing inks for the graphics industry, such as, for example, in paper, textile or decorative printing, and in the mass coloring of paper, for preparing inks, water-based or nonwater-based ink-jet inks, microemulsion inks, and inks which operate in accordance with the hot-melt process.

The compounds of the invention are also suitable for use as colorants in electrophotographic toners and developers, such as, for example, one- or two-component powder toners (also called one-or two-component developers), magnetic toners, liquid toners, polymerization toners and specialty toners.

Typical toner binders are addition polymerization resins, polyaddition resins and polycondensation resins, such as styrene, styrene-acrylate, styrene-butadiene, acrylate, polyester, phenol-epoxy resins, polysulfones, polyurethanes, individually or in combination, and also polyethylene and polypropylene, which may include further ingredients, such as charge control agents, waxes or flow assistants, or may be modified subsequently with these additions.

The compounds of the invention are additionally suitable for use as colorants in powders and powder coating materials, particularly in triboelectrically or electrokinetically sprayable powder coating materials which are employed to coat the surfaces or articles made, for example, of metal, wood, plastic, glass, ceramic, concrete, textile material, paper or rubber.

Typical powder coating resins used include epoxy resins, carboxyl- and hydroxyl-containing polyester resins, polyurethane resins and acrylic resins, together with customary hardeners. Resin combinations are also used. Thus, for example, epoxy resins are frequently used in combination with carboxyl- and hydroxyl-containing polyester resins. Typical hardener components (depending on the resin system) are, for example, acid anhydrides, imidazoles and also dicyandiamide and its derivatives, blocked isocyanates, bisacylurethanes, phenolic resins, melamine resins, triglycidyl isocyanurates, oxazolines and dicarboxylic acids.

Additionally the compounds of the invention are suitable for use as colorants in water-based and nonwater-based ink-jet inks and also in those inks which operate in accordance with the hot-melt process.

Ink-jet inks contain in general a total of 0.5% to 15%, preferably 1.5% to 8%, by weight (calculated on a dry basis) of one or more of the compounds of the invention.

Microemulsion inks are based on organic solvents, water and, if desired, an additional hydrotropic substance (interface mediator).

Microemulsion inks contain generally 0.5% to 15%, preferably 1.5% to 8%, by weight of one or more of the compounds of the invention, 5% to 99% by weight of water and 0.5% to 94.5% by weight of organic solvent and/or hydrotropic compound.

Solvent-based ink-jet inks contain preferably 0.5% to 15% by weight of one or more of the compounds of the invention, 85% to 99.5% by weight of organic solvent and/or hydrotropic compounds.

Hot-melt inks are based mostly on waxes, fatty acids, fatty alcohols or sulfonamides which are solid at room temperature and liquefy on heating, the preferred melting range being situated between about 60° C. and about 140° C. Hot-melt ink-jet inks are composed, for example, essentially of 20% to 90% by weight of wax and 1% to 10% by weight of one or more of the compounds of the invention. Additionally there may be 0% to 20% by weight of an additional polymer (as "dye dissolver"), 0% to 5% by weight of dispersing assistants, 0% to 20% by weight of viscosity modifiers, 0% to 20% by weight of plasticizers, 0% to 10% by weight of tack additive, 0% to 10% by weight of transparency stabilizer (which prevents, for example, the waxes crystallizing) and 0% to 2% by weight of antioxidant.

The colorants of the invention are also suitable, moreover, for use as color filters, both for additive and for subtractive color generation, and also as colorants for electronic inks ("e-inks") or electronic paper ("e-paper").

In the production of what are called color filters, both reflective and transparent color filters, pigments in the form of a paste or as pigmented photoresists in suitable binders (acrylates, acrylic esters, polyimides, polyvinyl alcohols, epoxides, polyesters, melamines, gelatin, caseins) are applied to the respective LCD components (e.g. TFT-LCD=thin film transistor liquid crystal displays or, e.g. ((S)TN-LCD=(super) twisted nematic-LCD). Besides high thermal stability, high pigment cleanness is a prerequisite for a stable paste or a pigmented photoresist.

Furthermore, the pigmented color filters may also be applied by ink-jet printing processes or other suitable printing processes.

The present invention provides, moreover, for the use of the colorants of the invention in optical layers, optical data storage, preferably for optical data storage where a laser is used to write the data. The solubility of the colorants in the application medium, which is needed for this application, can be adjusted by means of the nature and number of the substituents.

The compounds of the invention are, furthermore, suitable for use as colorants in cosmetics, for coloring seed, and for coloring mineral oils, lubricating greases, and waxes.

Depending on the nature of the substituents of the compounds of the invention the colorations obtained are distinguished by good heat fastness, light fastness and weather fastness, by chemical resistance and by the very good applications properties, e.g., crystallization fastness and dispersion fastness, and in particular by their migration fastness, bleed fastness, fastness to overcoating, and solvent fastness. The compounds used as polymer-soluble dyes naturally have only little, or restricted, solvent fastness.

The invention additionally provides a composition comprising an organic or inorganic material of high or low molecular mass, particularly organic material of high molecular mass, and at least one compound of the invention in a coloristically effective amount, generally in the range from 0.005% to 70% by weight, in particular from 0.01% to 10% by weight, based on the organic or inorganic material.

EXAMPLE 1

3,3'-Bis(1,3-diethyl-2-thio-4,6-dioxotetrahydropyrimidin-5-ylidene)-[1,1']biisoindolylidene 10 g of [1,1']biisoindolylidene-3,3'-diimine and 23.1 g of 1,3-diethyl-2-thio-barbituric acid are stirred in a mixture of 100 ml of NMP and 100 ml of glacial acetic acid at 155° C. for 4 hours. After cooling to room temperature the suspension is filtered and the filter product is washed with ethanol and then water and dried at 60° C. This gives 21.3 g (88%) of a metallic green powder of a compound of the following formula

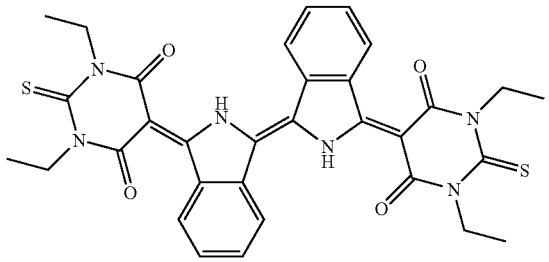

Melting point: >300° C. H-NMR ($D_2SO_4$): 8.05 (d, 2H), 7.80 (d, 2H), 7.54 (t, 2H), 7.33 (t, 2H), 3.95 (s, broad, 8H), 0.95 (t, 12H).

EXAMPLE 2

3,3'-Bis(1,3-dimethyl-2,4,6-trioxotetrahydropyrimidin-5-ylidene)-[1,1']biisoindolylidene 10 g of [1,1']biisoindolylidene-3,3'-diimine and 18.1 g of 1,3-dimethyl-barbituric acid are stirred in a mixture of 160 ml of NMP and 40 ml of glacial acetic acid at reflux for 5 hours. After cooling to room temperature the suspension is filtered and the filter product is washed with ethanol and then water and dried at 60° C. This gives 14.5 g (70%) of a virtually black powder of a compound of the following formula

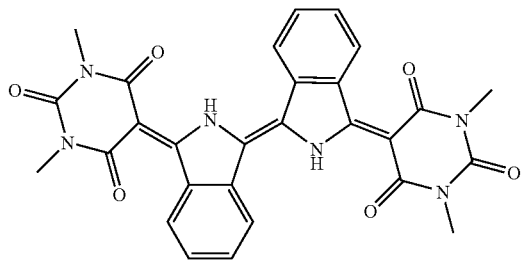

Melting point: >300° C. MS (m/e): 539 [M+H]$^+$, 561 [M+Na]$^+$

EXAMPLE 3

3,3'-Bis(1,3-bis(2-ethylhexyl)-2,4,6-trioxotetrahydropyrimidin-5-ylidene)-[1,1']biisoindolylidene 10 g of [1,1']biisoindolylidene-3,3'-diimine and 40.9 g of 1,3-bis(2-ethyl-hexyl)barbituric acid are stirred in a mixture of 100 ml of NMP and 100 ml of glacial acetic acid at 155° C. for 4 hours. After cooling to room temperature the suspension is filtered and the filter product is washed with ethanol and then water and dried at 60° C. This gives 28.8 g (80%) of a violet powder of a compound of the following formula

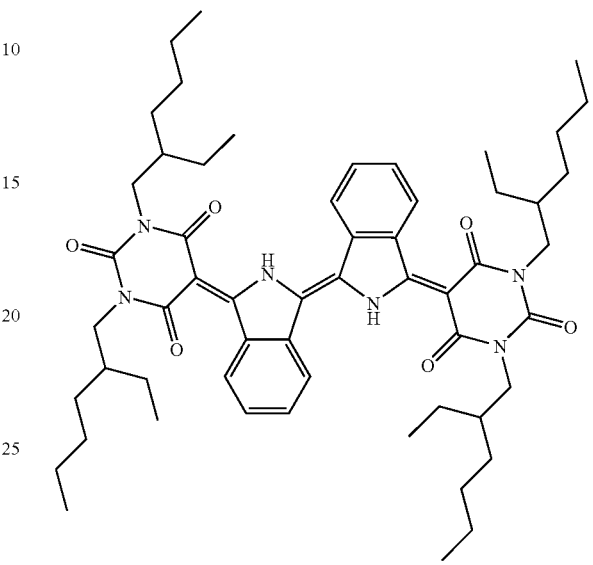

Melting range: 198-206° C. MALDI (m/e, negative mode): 930 [M-H]$^-$ H-NMR (CDCl$_3$): 15.14 (s, 2H), 9.62 (d, 2H), 8.43 (d, 2H), 7.88 (t, 2H), 7.71 (t, 2H), 4.04 (m, 8H), 1.94 (m, 4H), 1.35 (m, 32H), 1.14 (m, 24H)

EXAMPLE 4

3,3'-Bis(1,3-diphenyl-2,4,6-trioxotetrahydropyrimidin-5-ylidene)-[1,1']biisoindolylidene 19.4 g of [1,1']biisoindolylidene-3,3'-diimine and 50.0 g of 1,3-diphenyl-barbituric acid are stirred in a mixture of 230 ml of NMP and 350 ml of glacial acetic acid at reflux for 6 hours. After cooling to room temperature the suspension is filtered and the filter product is washed with ethanol and then water and dried at 60° C. This gives 48.1 g (82%) of a violet powder of a compound of the following formula

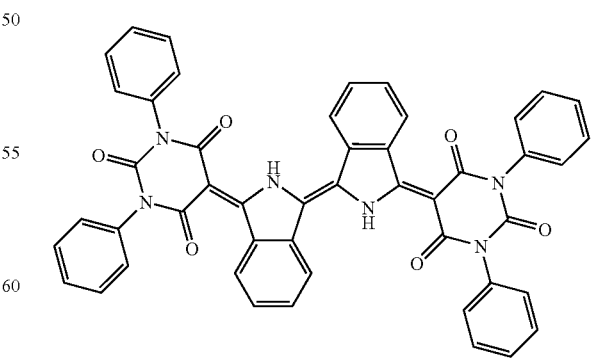

Melting point: >300° C. MS (m/e): 787 [M+H]$^+$, 809 [M+Na]$^+$ H-NMR ($D_2SO_4$): 7.63 (d, 2H), 7.27 (d, 2H), 7.14 (t, 2H), 6.97 (t, 2H), 6.82 (m, 12H), 6.65 (d, 8H).

EXAMPLE 5

3,3'-Bis(1,3-dioxoindan-2-ylidene)-[1,1']biisoindolylidene 10.0 g of [1,1']biisoindolylidene-3,3'-diimine and 16.9 g of 1,3-dioxoindane are stirred in a mixture of 100 ml of NMP and 100 ml of glacial acetic acid at reflux for 6 hours. After cooling to room temperature the suspension is filtered, the filter product is washed with a mixture of NMP and glacial acetic acid (1:1), subsequently ethanol and then water and dried at 60° C. This gives 10.8 g (54%) of a black powder of a compound of the following formula

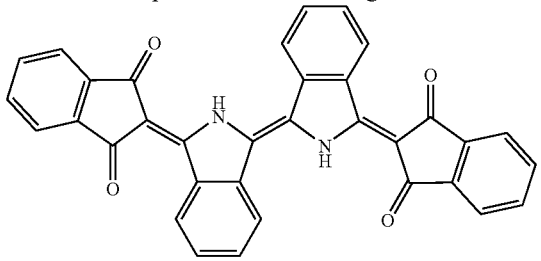

Melting point: >300° C. MS (m/e): 519 [M+H]$^+$

COMPARATIVE EXAMPLE 1

3,3'-Bis(2,4-dioxo-1,4-dihydro-2H-quinolin-3-ylidene)-[1,1']biisoindolylidene 5.0 g of [1,1']biisoindolylidene-3,3'-diimine and 14.9 g of 1H-quinoline-2,4-dione are stirred in a mixture of 90 ml of NMP and 10 ml of glacial acetic acid at reflux for 6 hours. After cooling to room temperature the suspension is filtered and the filter product is washed with ethanol and then water and dried at 60° C. This gives 6.2 g (59%) of a virtually black powder of a compound of the following formula

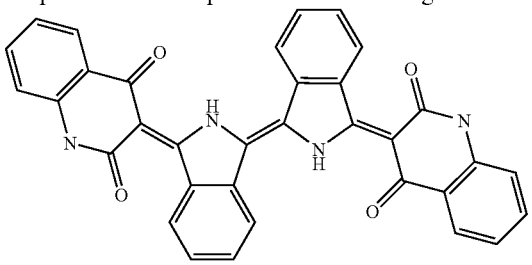

Melting point: >300° C. MALDI (m/e): 547 [M-H]$^-$

COMPARATIVE EXAMPLE 2

3,3'-Bis(3-methyl-5-oxo-1-(3-carboxyphenyl)-1,5-dihydropyrazol-4-ylidene)-[1,1']biisoindolylidene 10.0 g of [1,1']biisoindolylidene-3,3'-diimine and 25.3 g of 3-methyl-1-(3-carboxyphenyl)-2-pyrazolin-5-one are stirred in a mixture of 160 ml of NMP and 40 ml of glacial acetic acid at reflux for 5 hours. After cooling to room temperature the suspension is filtered and the filter product is washed with ethanol and then water and dried at 60° C. This gives 21.7 g (85%) of a brownish black powder of a compound of the following formula

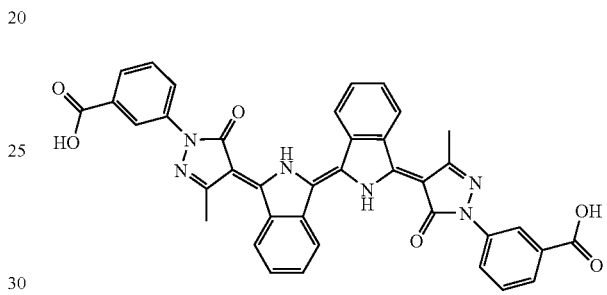

Melting point: >300° C. MS (m/e): 661 [M-H]$^-$

COMPARATIVE EXAMPLE 3

3,3'-Bis(3-methyl-5-oxo-1-(3-sulfamoylphenyl)-1,5-dihydropyrazol-4-ylidene)-[1,1']biisoindolylidene 10.0 g of [1,1']biisoindolylidene-3,3'-diimine and 29.4 g of 3-methyl-1-(3-sulfamoyl)-2-pyrazolin-5-one are stirred in a mixture of 240 ml of NMP and 60 ml of glacial acetic acid at reflux for 3 hours. After cooling to room temperature the suspension is filtered and the filter product is washed with ethanol and then water and dried at 60° C. This gives 26.7 g (95%) of a brownish black powder of a compound of the following formula

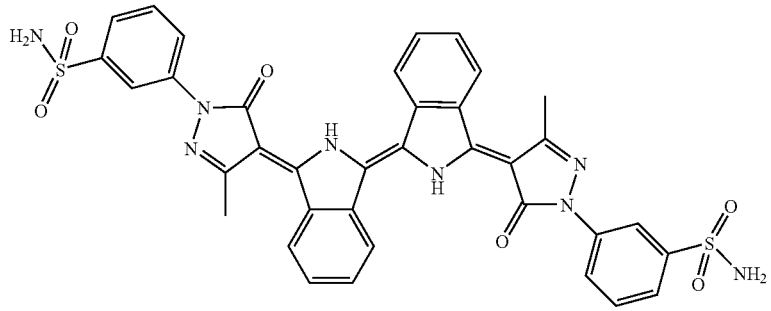

Melting point: >300° C. MALDI (m/e): 731 [M-H]⁻

APPLICATION EXAMPLES

To assess the properties of the pigments prepared in accordance with the invention in the coatings sector a selection was made, from among the multiplicity of known varnishes, of an aromatics-containing alkyl-melamine resin varnish (AM) based on a medium-oil alkyd resin and on a butanol-etherified melamine resin, and also of an aromatics-free, air-drying alkyd resin varnish (LA) based on a long-oil soya alkyd resin.

To assess the properties of the polymer-soluble dyes of the invention, glass-clear polystyrene, polycarbonate or polyester were selected as plastics for coloring. Test specimens were produced by injection molding.

APPLICATION EXAMPLE 1

Application of the pigment from example 1 in LA varnish produces strongly colored coatings which in the masstone are a hiding black and in the white reduction are reddish blue.

APPLICATION EXAMPLE 2

Application of the pigment from example 2 in LA varnish produces strongly colored coatings which in the masstone are a hiding black and in the white reduction are reddish violet.

APPLICATION EXAMPLE 3

Application of the pigment from example 3 in polystyrene produces in both the masstone and the white reduction clean and strongly colored violet test specimens.

APPLICATION EXAMPLE 4

Application of the pigment from example 3 in polyethylene terephthalate produces in both the masstone and the white reduction clean and strongly colored violet test specimens.

APPLICATION EXAMPLE 5

Application of the pigment from example 5 in AM varnish produces clean and strongly colored coatings which in the masstone are a dark violet and in the white reduction are reddish violet.

APPLICATION EXAMPLE 6

Application of the pigment from example 4 in polycarbonate produces in both the masstone and the white reduction strongly colored, reddish violet test specimens, with red fluorescence in the masstone.

COMPARATIVE APPLICATION EXAMPLE 1

Application of the pigment from comparative example 1 in the AM varnish produces coatings which in the masstone are a hiding black and in the white reduction are bluish violet, these coatings being significantly duller than those with compounds of examples 1 to 5.

COMPARATIVE APPLICATION EXAMPLE 2

Application of the pigment from comparative example 2 in the AM varnish produces coatings which in the masstone are a hiding black and in the white reduction are violet, these coatings being significantly duller than those with compounds of examples 1 to 5.

COMPARATIVE APPLICATION EXAMPLE 3

Application of the pigment from comparative example 3 in the AM varnish produces strongly colored coatings which in the masstone are a hiding black and in the white reduction are blue, these coatings being significantly duller than those with compounds of examples 1 to 5.

The invention claimed is:

1. A compound of the formula (I)

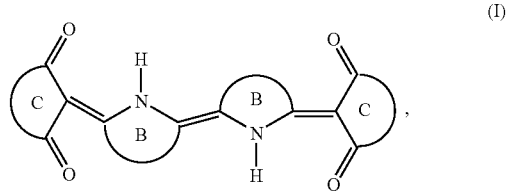

wherein C is of the formula (a)

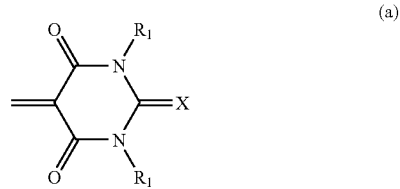

wherein $R_1$ independently of one another are hydrogen, $C_1$-$C_{25}$alkyl, $C_5$-$C_{12}$ cycloalkyl, $C_6$-$C_{24}$aryl, $C_1$-$C_{25}$ alkyl-($C_6$-$C_{10}$)-aryl, a heteroaromatic radical having 1, 2 or 3 heteroatoms selected from the group consisting of N, O and S, —(CH$_2$)$_n$—COR$_3$ and —(CH$_2$)$_m$—OR$_4$, in which $R_3$ is hydroxyl, unsubstituted or mono- or poly-hydroxyl- or amino-substituted $C_1$-$C_{25}$ alkoxy, $C_1$-$C_{25}$ alkylamino, di-($C_1$-$C_{25}$ alkyl)amino, $C_1$-$C_{25}$ alkyl-$C_6$-$C_{24}$ arylamino, ($C_6$-$C_{24}$aryl)amino di-($C_6$-$C_{24}$aryl)amino or $C_2$-$C_{24}$ alkenyloxy, and $R_4$ is hydrogen or —CO—($C_1$-$C_{25}$ alkyl) and n and m independently of one another are an integer from 0 to 6, and wherein in $R_1$, $R_3$ and $R_4$ a C—C unit can, optionally be replaced by an ether unit C-O-C, and B is ortho-phenylene.

2. A compound as claimed in one claim 1, wherein $R_1$ is identical or different and is hydrogen, $C_1$-$C_{18}$ alkyl, benzyl, $C_5$-$C_6$ cycloalkyl, $C_6$-$C_{10}$ aryl, pyridyl, pyrryl, thienyl, imidazolyl, oxazolyl, thiazolyl, pyrimidyl, hydroxycarbonyl-$C_0$-$C_{10}$ alkyl, $C_1$-$C_{18}$ alkoxycarbonyl-$C_0$-$C_{18}$ alkyl, aminocarbonyl-$C_0$-$C_{18}$ alkyl, di($C_1C_{18}$ alkyl)-aminocarbonyl-$C_0$-$C_{18}$ alkyl, $C_1C_{-18}$ arylaminocarbonyl-$C_0$-$C_{18}$ alkyl, di($C_1$ $C_{-18}$ alkyl)-aminocarbonyl-$C_0$-$C_{18}$ alkyl, alkyl-$C_6$-$C_{10}$-arylaminocarbonyl-$C_0$-$C_{18}$ alkyl or di($C_6$-$C_{10}$-aryl)-aminocarbonyl-$C_0$-$C_{18}$ alkyl.

3. A compound as claimed in claim 1, wherein the compound of formula (I) is of the formula (2)

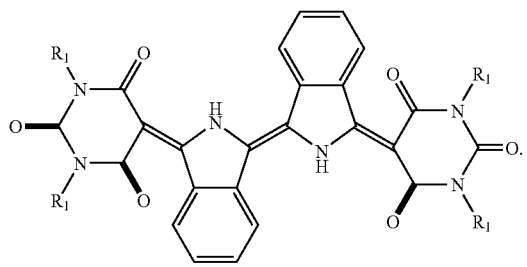

(2)

4. A process for preparing a compound as claimed in claim 1, comprising the step of condensing a compound of the formula (III)

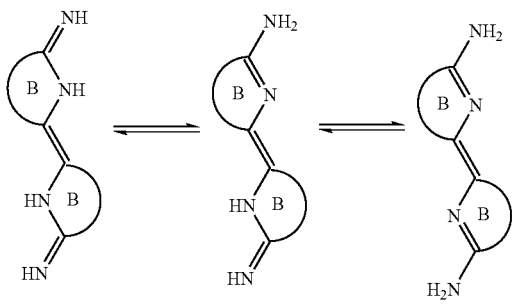

(III)

with at least 2 mole equivalents of a cyclic compound of the formula (IV)

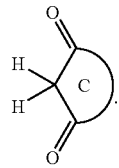

(IV)

5. A composition comprising a compound as claimed in claim 1, wherein the composition is in the form of a oil-based paint water-based paint, varnish, camouflage paint, spin colored article, plastic, printing ink, colored paper, colored seed, powder coating material, ink jet ink, microemulsion ink or hot melt process ink.

6. A colorant for electrophotographic toners, electrophotographic developers or electronic inks comprising a compound as claimed in claim 1.

7. A compound as claimed in claim 1, wherein n and m independently of one another are 1 to 4.

8. An optical layer for optical data storage comprising a compound as claimed in claim 1.

9. A color filter comprising a compound as claimed in claim 1.

* * * * *